United States Patent [19]

Lombardino et al.

[11] Patent Number: 4,656,265
[45] Date of Patent: Apr. 7, 1987

[54] CYCLIC PRODRUGS OF ANTIINFLAMMATORY OXICAMS

[75] Inventors: Joseph G. Lombardino, Niantic; Anthony Marfat, Groton, both of Conn.

[73] Assignee: Pfizer Inc., New York, N.Y.

[21] Appl. No.: 623,251

[22] Filed: Jun. 21, 1984

[51] Int. Cl.$^4$ .................. C07D 413/14; C07D 417/14
[52] U.S. Cl. .................................................... 544/33
[58] Field of Search ........................ 544/33; 514/222

[56] References Cited

U.S. PATENT DOCUMENTS

| | | | |
|---|---|---|---|
| 3,492,298 | 1/1970 | Rasmussen | 544/33 |
| 3,591,584 | 7/1971 | Lombardino | 260/243 |
| 3,787,324 | 1/1974 | Zinnes et al. | 260/243 R |
| 3,822,258 | 7/1974 | Zinnes et al. | 260/243 R |
| 3,923,801 | 12/1975 | Rasmussen | 260/243 R |
| 4,180,662 | 12/1979 | Pfister et al. | 544/48 |
| 4,309,427 | 1/1982 | Lombardino | 424/246 |
| 4,376,768 | 3/1983 | Ozaki et al. | 424/246 |
| 4,563,452 | 1/1986 | Soler | 514/222 |

FOREIGN PATENT DOCUMENTS 0099770 2/1984 European Pat. Off. .
2528433 12/1983 France .

OTHER PUBLICATIONS

Zinnes et al., J. Med. Chem., 16, 44–48 (1973).
Del Favero, "Side Effects of Drugs Annual 7", Dukes and Elis, Eds. Excerpta Medica, Amsterdam, 1983, pp. 104–105.

*Primary Examiner*—John M. Ford
*Attorney, Agent, or Firm*—Charles J. Knuth; Albert E. Frost; Paul D. Thomas

[57] ABSTRACT

Compounds of the formula

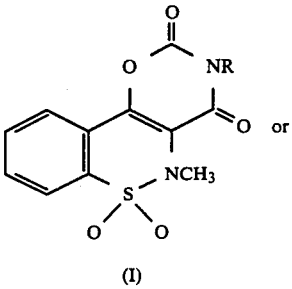

(I)

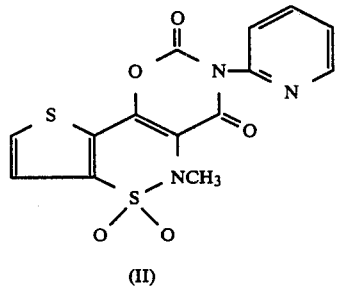

(II)

or a pharmaceutically acceptable acid addition salt thereof wherein R is 2-pyridyl, 6-chloro-2-pyridyl, 6-methyl-2-pyridyl or 5-methylisoxazol-3-yl; useful as prodrug forms of the corresponding known oxicam antiinflammatory and analgesic agents, piroxicam, the corresponding 6-chloro-2-pyridyl and 6-methyl-2-pyridylcarboxamides, isoxicam and tenoxicam; methods for their use, pharmaceutical compositions containing them and a process for their preparation.

7 Claims, No Drawings

CYCLIC PRODRUGS OF ANTIINFLAMMATORY OXICAMS

BACKGROUND OF THE INVENTION

The present invention is concerned with certain novel oxazino[5,6-c]1,2-benzothiazine, 6,6-dioxides and oxazino[5,6-c]1,2-thienothiazine 6,6-dioxides of the formula.

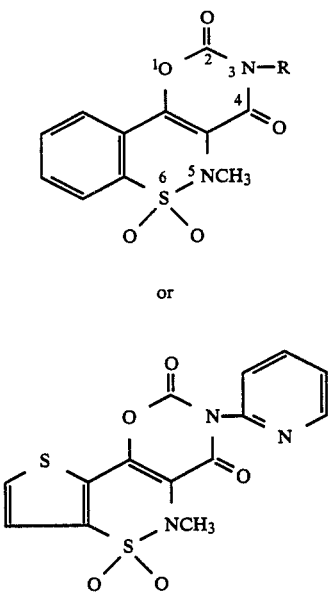

which are useful oral prodrugs of the nonsteroidal antiinflammatory and analgesic oxicams from which they are derived.

The pertinent oxicams and their utility as antiinflammatory and analgesic agents are disclosed in U.S. Pat. Nos. 3,591,584; 3,787,324; 3,822,258; 4,180,662 and 4,376,768. U.S. Pat. No. 4,309,427 discloses certain ester derivatives of piroxicam, N-(2-pyridyl)-4-hydroxy-2-methyl-2H-1,2-benzothiazine-3-carboxamide 1,1-dioxide, and its N-(6-methyl-2-pyridyl) analog which are useful antiinflammatory agents, especially for topical administration. J. Med. Chem., 16, 44–48 (1973) discloses N-phenyl-4-acetoxy-2-methyl-2H-1,2-benzothiazine-3-carboxamide 1,1-dioxide as having moderate antiinflammatory activity while the corresponding 4-hydroxy compound had marked activity.

U.S. Pat. No. 3,923,801 discloses 5-methyl-3-aryl-2H,5H-1,3-oxazino[5,6-c]1,2-benzothiazine-2,4(3H)-dione 6,6-dioxides having inflammitory properties wherein the 3-aryl group is selected from phenyl and substituted phenyl. The compounds of this reference were prepared by reaction of the appropriate 2-methyl-4-hydroxy-2H-benzothiazine-3-carboxanilide 1,1-dioxide with e.g., a chloroformic ester, such as ethyl chloroformate, in the presence of an alkali metal base and contacting the resulting intermediate (III)

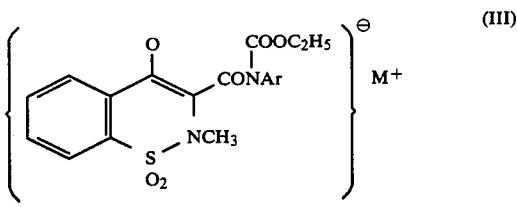

wherein Ar is phenyl or substituted phenyl amd M+ is an alkali metal cation, with an acid to affect cyclization.

SUMMARY OF THE INVENTION

The present invention provides cyclic prodrugs of antiinflammatory and analgesic oxicams of the formulae

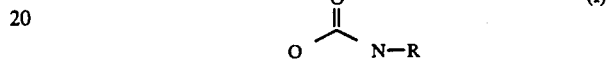
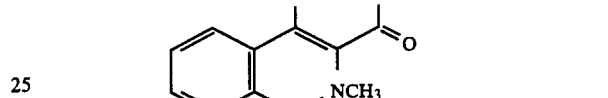

and

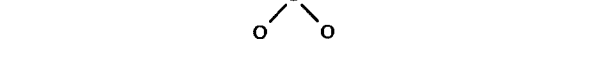
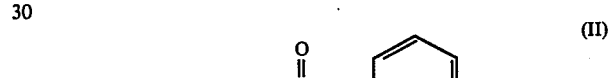

wherein R is 2-pyridyl, 6-chloro-2-pyridyl, 6-methyl-2-pyridyl or 5-methylisoxazol-3-yl. An especially preferred compound of formula (I) is that in which R is 2-pyridyl which is derived from piroxicam.

The prodrugs of the present invention are not enolic acids and they therefor show reduced gastric irritation when compared with the parent oxicams which are enolic acids.

The term "prodrug" refers to compounds which are drug precursors which, following administration and absorption, release the drug in vivo via some metabolic process such as hydrolysis.

The present invention also encompasses pharmaceutical compositions suitable for administration to a warm-blooded animal, including a human, which comprises a pharmaceutically acceptable carrier and an antiinflammatory effective amount of a compound of formula (I) or (II), and a method of treating an inflammatory condition in a warm-blooded animal in need of such treatment by administering an antiinflammatory effective amount of a compound of formula (I) or (II).

While all of the usual routes of administration are useful with the invention compounds, the preferred route of administration is oral. After gastrointestinal absorption, the present compounds are hydrolyzed in vivo, to the corresponding oxicams of formula (IV) or (V) or a salt thereof,

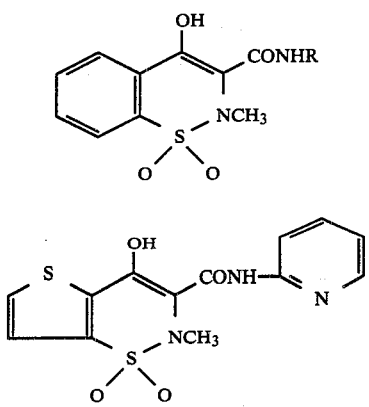

wherein R is as defined above for compounds of formula I. Since the prodrugs of the invention are not enolic acids, exposure of the gastrointestinal tract to the acidic oxicams compound is thereby minimized. Further, since gastrointestinal complications have been noted as a major adverse reaction of acid non-steroidal antiinflammatory drugs [see e.g., Del Favero in "Side Effects of Drugs Annual 7", Dukes and Elis, Eds. Excerpta Medica, Amsterdam, 1983, p. 104–105], the invention compounds (I) and (II) have a distinct advantage over the parent enolic oxicams.

The present invention also provides a novel process for preparation of the valuable prodrugs of formula (I) or (II) by reaction of the appropriate oxicam of formula (IV) or (V) with at least an equimolar amount of a cyclizing agent of the formula $R^1COCl$ in the presence of reaction inert solvent and from one to two equivalents of an acid binding agent at a temperature of from $-70°$ to $50°$ C.

While phosgene, $R^1COCl$ where $R^1$ is Cl, is the most preferred cyclizing reagent, other reagents such as those wherein $R^1$ is $(C_1-C_4)$alkoxy, phenoxy, benzyloxy or trichloromethoxy are also effective. An especially preferred acid binding agent is triethylamine and methylene dichloride is an especially preferred solvent.

DETAILED DESCRIPTION OF THE INVENTION

The novel process for preparation of the prodrugs of formula (I) or (II) is carried out employing the appropriate oxicam of the formula (IV) or (V) as starting material and the cyclization is carried out in a single step under mild conditions. By contrast, the method disclosed in U.S. Pat. No. 3,923,801 requires several steps and reagents.

Ordinarily, the invention process is carried out by reacting the appropriate oxicam (IV) or (V), in the presence of a reaction-inert solvent and from one to two molar equivalents of an acid binding agent, with a cyclizing agent of the formula $R^1COCl$, where $R^1$ is Cl, $(C_1-C_4)$alkoxy, phenoxy, benzyloxy or trichloromethoxy, in an amount which is at least equimolar with the starting compound (IV) or (V), at a temperature of from $-70°$ to $50°$ C.

Examples of suitable reaction inert organic solvents for use in the invention process included acyclic hydrocarbons such as pentane, hexane and heptane; cyclic hydrocarbons such as cyclopentane and cyclohexane; aromatic hydrocarbons such as benzene, toluene and xylene; halogenated hydrocarbons such as methylene dichloride, 1,2-dichloroethane, chloroform, carbon tetrachloride and 1,2-dibromoethane; ethers such as ethyl or isopropyl ether and tetrahydrofuran; and ethyl acetate, acetonitrile, dimethylformamide or dimethylsulfoxide. Particularly preferred such solvents are toluene, methylene dichloride, ethyl ether, tetrahydrofuran and ethyl acetate, and methylene dichloride is especially preferred for reasons of economy and efficiency.

Suitable acid binding agents for use in the invention process are those basic compounds which will bind the hydrogen chloride formed in the reaction but will not form an unwanted by-product with the reagent $R^1COCl$ or compounds (IV) or (V) under the conditions employed. Examples of suitable acid binding agents include tertiary amines such as the trialkylamines having from 3 to 30 carbon atoms, dialkyl aryl amines and alkyl diaryl amines having 8 to 30 carbon atoms, aralkyl dialkyl amines having from 9 to 30 carbon atoms, N-alkyl heterocyclic amines having from 6 to 25 carbon atoms; alkali metal or alkaline earth carbonates or bicarbonates, and alkaline earth oxides or hydroxides. Particularly preferred acid binding agents are sodium bicarbonate, calcium carbonate, calcium oxide, N,N-dimethylaniline, N-methylmorpholine and N-methylpiperidine. Most particularly preferred is triethylamine.

In theory the cyclizing agent, $R^1COCl$, and the starting compound of formula (IV) or (V) are required in equimolar amounts to form the desired, respective products of formula (I) or (II). In practice however, a molar excess of the cyclizing agent is ordinarily employed in order to ensure completion of reaction and to minimize the formation of unwanted by-products. Typically, a molar excess of from about 1 to 10 times is employed with good results.

While the invention process will proceed satisfactorily by addition of the cyclizing agent to a solution of the starting oxicam (IV) or (V) and acid binding agent in reaction inert solvent, it is preferred that the addition is carried out in the inverse order, that is, the solution of starting oxicam and acid binding agent is added to the cyclizing agent maintained at the desired temperature.

As mentioned above the preferred reaction temperature is in a range of from $-70°$ to $50°$ C. An especially preferred temperature is in the range of from $-30°$ to $50°$ C. and most particularly from $0°$ to $25°$ C.

Under the mild conditions of the invention process the desired products are readily formed in a short time, i.e., in from about 30 minutes to four hours, and are isolated and purified by standard methods well known to those of skill in the art. For example, the desired product is obtained by filtration of the reaction mixture, washing the collected solid with solvent to remove impurities. The crude products are readily purified, e.g., by recrystallization or column chromato-graphy.

The cyclic prodrugs of formula (I) and (II) are not acidic since the enolic oxygen is esterified. However, the invention compound (II) and compounds of formula (I) having a basic nitrogen atom in R are capable of forming acid addition salts and such salts with pharmaceutically acceptable acids are included in the invention. Examples of such acids are hydrochloric, benzosulfonic, p-toluenesulfonic, 2-naphthalenesulfonic, hydrobromic and phosphoric acids.

The oxicams of formula (IV) or (V) required as starting materials for the invention process are available by methods well known in the art; see, for example, the references to oxicams cited above. The cyclizing agents of formula R¹COCl and other reagents and solvents required in the invention process are available commercially.

The cylic prodrugs of formula (I) and (II) are evaluated for their antiinflammatory activity according to known methods by administering multiple oral doses in model tests such as the rat foot edema test, rat adjuvant-induced arthritis test or phenylbenzoquinone-induced writhing test in mice, as previously used in the evaluation of the parent oxicams and described in the references cited above and elsewhere in the literature; see e.g., C. A. Winter, in "Progress in Drug Research" edited by E. Jucker, Birkhauser Verlag, Basel, Vol. 10, 1966, pp. 139–192.

In comparison with the parent oxicams of formula (IV) and (V), the novel prodrugs of formula (I) and (II) are found to have markedly reduced ability to inhibit prostagladin synthesis from arachidonic acid in tests carried out by a modification of the method of T. J. Carty et. al., *Prostaglandins*, 19, 51–59 (1980). In the modified procedure cultures of rat basophilic leukemic cells (RBL-1), prepared by the method of Jakschik et. al., ibid., 16. 733 (1978), are employed in place of mouse fibroblast (MC5-5) and rabbit synovial cell cultures. Thus, the invention compounds themselves are relatively inactive as antiiflammatory agents, but they give rise to an active antiinflammatory compounds upon hydrolysis in vivo. Since the compounds (I) and (II) are not enolic acids and it is known that the hydrolysis takes place after the prodrug leaves the stomach, they will significantly reduce the gastric irritation caused by oral administration of the parent enolic oxicams.

On a molar basis, the present oxicam prodrugs are generally dosed at the same level and frequency as the known oxicams from which they are derived. However, the non-enolic nature of the present compounds will generally permit higher tolerated oral doses, when such higher dosage is required in the control of inflammation.

In general the invention compounds are administered via either the oral, parenteral or topical routes in doses ranging from about 10 mg. up to about 1000 mg. per day, although variations will necessarily occur depending upon the weight and condition of the subject being treated and the particular route of administration chosen. However, a dosage level that is in the range of from about 0.16 mg. to about 16 mg. per kg. of body weight per day is most desirably employed. Nevertheless, variations may occur depending upon the species of animal being treated and its individual response to said medicament, as well as on the type of pharmaceutical formulation and the time period and interval at which such administration is carried out. In some instances, dosage level below the lower limit of the aforesaid range may be more than adequate, while in other cases still larger doses may be employed without harmful side effects provided that such higher dose levels are first divided into several smaller doses for administration throughout the day.

The present oxicam prodrugs are also formulated in the same manner, and administered by the same routes as the known oxicams, as described in the above cited references. The preferred route of administration is oral, thus taking particular advantage of the nonenolic nature of the present compounds.

The present invention is illustrated by the following examples, but is not limited to the specific details of these examples.

EXAMPLE 1

5-Methyl-3-(2-pyridyl)-2H,5H-1,3-oxazino[5,6-c]1,2-benzothiazine-2,4-(3H)-dione 6,6-dioxide; [(I), R=2-pyridyl]

To a solution of 5.0 g, (15 mmole) N-(2-pyridyl) 4-hydroxy-2-methyl-2H-1,2-benzothiazine-3-carboxamide 1,1-dioxide (piroxicam) in 100 ml. dry methylene dichloride was added 2.5 ml. (16.5 mmole) anhydrous triethylamine at room temperature. The resulting solution was added dropwise under a nitrogen atmosphere to an ice-cold solution of 5.0 g. (50 mmole) phosgene in 80 ml. methylene dichloride. After the addition was completed, the mixture was stirred at 0° C. for one hour, then at room temperature for 15 minutes. The precipitated solid was collected by filtration, washed in turn with methylene dichloride, ethyl acetate, water and hexane. The washed solid was dried in air to afford 3.0* g. (56%) of the product which was homogeneous as determined by silica gel thin-layer chromatography ($R_f$ 0.4, methylene dichloride/ethyl acetate, 80/20). A sample was recrystallized from acetone, M.P. 263°–265° C.
*A significant amount of product was lost due to washing with methylene dichloride and ethyl acetate as the product is somewhat soluble in these solvents and their mixtures.

Mass spectrum (high resolution) M/e: M+ 357.0359 (Theory 357.0410).

Infrared spectrum (KBr) cm⁻¹: 1710 and 1790. 250 MHz ¹H-NMR(CDCl₃), ppm (delta): 3.22 (s, 3H), 7.2–8.1 (m,8H).

Analysis Calculated for $C_{16}H_{11}N_2O_5S$: Found: C, 53.78; H, 3.10; N, 11.76. C, 53.66; H, 3.26; N, 11.74.

EXAMPLE 2

5-Methyl-3-(6-methyl-2-pyridyl)-2H,5H-1,3-oxazino[5,6-c] 1,2-benzothiazine-2,4-(3H)-dione 6,6-dioxide; [(I), R-6-methyl-2-pyridyl]

A mixture of 3.37 g. (10 mmole) N-(6-methyl-2-pyridyl) 4-hydroxy-2-methyl-2H-1,2-benzothiazine-3-carboxamide 1,1-dioxide, 100 ml. chloroform and 1.01 g. (10 mmole) N-methylmorpholine is stirred to effect solution. This is added dropwise to a solution of 3.0 g. (15 mmole) of trichloromethyl chloroformate in 50 ml. chloroform at −20° C. over 10 minutes and the resulting mixture allowed to warm to 30° C. at which temperature some refluxing takes place. The mixture is stirred at 30° C. for one hour then warmed to 50° C. and held at this temperature for an hour. The reaction mixture is concentrated in vacuo to about half-volume and filtered to remove precipitated product, which is purified by recrystallization.

EXAMPLE 3

5-Methyl-3-(6-chloro-2-pyridyl)-2H,5H-1,3-oxazino [5,6-c] 1,2-benzothiazine-2,4-(3H)-dione 6,6-dioxide; [(I), R=6-chloro-2-pyridyl]

The procedure of Example 1 is repeated on a 20 millimolar scale with N-(6-chloro-2-pyridyl-4-hydroxy-2-methyl-2H-1;2-benzothiazine-3-carboxamide, sodium bicarbonate in tetrahydrofuran as solvent and ethyl chloroformate as cyclizing agent. The addition is carried out at −30° C., for 10 to 30 minutes the resulting mixture is then stirred at room temperature for five hours. The product is isolated and purified as described above.

When the above procedure is repeated, but with methyl chloroformate, isopropyl chloroformate, n- butyl chloroformate, t-butyl chloroformate, phenyl chloroformate or benzyl chloroformate as cyclizing agent the title compound is obtained in like manner.

EXAMPLE 4

5-Methyl-3-(5-methylisoxazol-3-yl)2H,5H-1,3-oxazino-[5,6-c] 1,2-benzothiazine-2,4-(3H)-dione 6,6-dioxide; [(I), R=5-methylisoxazol-3-yl]

To a solution of 10.05 g. (0.030 mmole) N-(5-methylisoxazol-3-yl) 4-hydroxy-2-methyl-2H-1,2-benzothiazine-3-carboxamide 1,1-dioxide (isoxicam) in 250 ml. methylene chloride is added 6.0 g. (0.06 mmole) N-methylpiperidine. The resulting solution is added dropwise under a nitrogen atmosphere to a solution of 5.0 g. (0.05 mmole) phosgene in 80 ml. methylene chloride at −70° C. When the addition is completed the mixture is allowed to warm to room temperature and stirred for two hours. The product is then isolated by filtration, washed with solvent and dried.

EXAMPLE 5

5-Methyl-3-(2-pyridyl)-2H,5H-1,3-oxazino-[5,6-c] thieno[2,3-e] 1,2-thiazine-2,4-(3H)-dione 6,6-dioxide hydrochloride; (II)

To a solution of 3.37 g. (10 mmole) N-(2-pyridyl)-4-hydroxy-2-methyl-2H-thieno[2,3-e]-1,2-thiazine-3-carboxamide 1,1-dioxide (tenoxicam) in 150 ml. toluene under nitrogen is added 1.01 g. (10 mmole) triethylamine and the mixture is cooled to 0° C. The cold solution is then added dropwise to a solution of 1.0 g. (10 mmole) phosgene in 50 ml. toluene at −70° C. over 45 minutes and stirring is continued at −70° to −60° C. for an additional 30 minutes. The reaction mixture is allowed to warm to room temperature and stirred for an hour. The solvent is evaporated in vacuo, the residue triturated with acetone and filtered to obtain the desired product which is purified by recrystallization, e.g., from acetine, ethanol or chloroform.

EXAMPLE 6

5-Methyl-3-(2-pyridyl)-2H,5H-1,3-oxazino[5,6-c]

thieno[2,3-e] 1,2-thiazine-2,4-(3H)-dione 6,6-dioxide; (II)

A mixture of 3.37 g. (10 mmole) N-(2-pyridyl)-4-hydroxy-2-methyl-2H-thieno[2,3-e]-1,2-thiazine-3-carboxamide 1,1-dioxide (tenoxicam) in 100 ml. 1,2-dichloroethane and 2.50 g. (21 mmole) N,N-dimethylaniline is stirred under nitrogen to affect solution, then cooled to 0° C. The resulting cold solution is added dropwise to a solution of 4.0 g. (20 mmole) trichloromethyl chloroformate in 100 ml. 1,2-dichloroethane maintained at 0° C. under nitrogen. After the addition is completed, the reaction mixture is stirred at 0°–10° C. for one hour then at room temperature for 30 minutes. The precipitated solid is collected by filtration, washed with methylene dichloride, water, hexane and air dried.

When the above reaction is carried out in benzene, methylene dichloride, ethyl ether, tetrahydrofuran, or ethyl acetate as solvent the results are substantially unchanged with.

When the above procedure is carried out, but with sodium bicarbonate, calcium oxide, triethylamine, N-methylmorpholine or N-methylpiperidine in place of N,N-dimethylaniline as acid binding agent, similar results are obtained.

We claim:

1. The compound of the formula

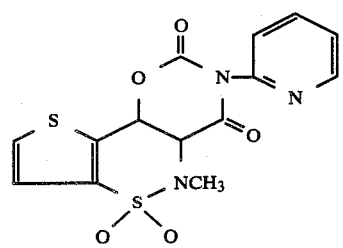

or a pharmaceutically acceptable acid addition salt thereof.

2. A process for preparation of a compound of the formula

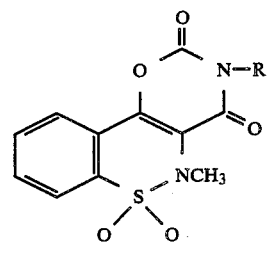

or

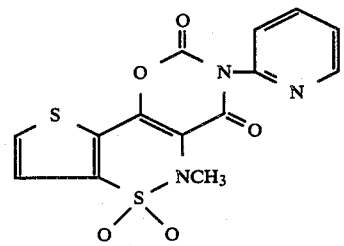

wherein R is 2-pyridyl, 6-chloro-2-pyridyl, 6-methyl-2-pyridyl or 5-methylisoxazol-3-yl, which comprises reacting a compound of the formula

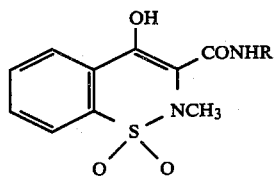

or

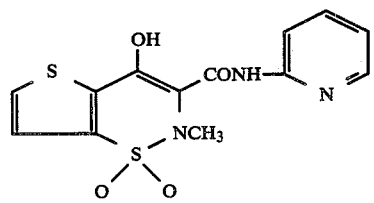

with at least an equimolar amount of a compound of the formula $R^1COCl$ where $R^1$ is Cl, $(C_1-C_4)$alkoxy, phenoxy, benzyloxy or trichloromethoxy in the presence of a reaction inert organic solvent and one to two molar equivalents of an acid binding agent at a temperature of from −70° to 50° C.

3. A process according to claim 2 wherein $R^1$ is Cl and said temperature is from −30° to 50° C.

4. A process according to claim 2 wherein said acid binding agent is triethylamine.

5. A process according to claim 2 wherein said solvent is methylene chloride.

6. A process according to claim 2 wherein a compound of the formula

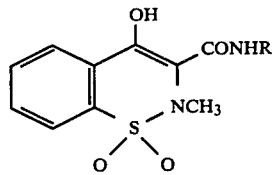

where R is 2-pyridyl is reacted with phosgene in the presence of methylene chloride at a temperature of from 0° to 25° C.

7. A process according to claim 6 wherein triethylamine is employed as acid binding agent and a molar excess of phosgene is employed.

* * * * *